United States Patent
Komatsu et al.

(10) Patent No.: US 8,776,577 B2
(45) Date of Patent: Jul. 15, 2014

(54) GENERATED GAS COLLECTING METHOD AND MEASURING METHOD

(75) Inventors: Akihiro Komatsu, Ome (JP); Takahiro Imamura, Ome (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 12 days.

(21) Appl. No.: 13/366,101

(22) Filed: Feb. 3, 2012

(65) Prior Publication Data

US 2012/0304739 A1 Dec. 6, 2012

(30) Foreign Application Priority Data

May 31, 2011 (JP) ................................. 2011-122780

(51) Int. Cl.
*G01N 25/00* (2006.01)
*B01D 53/02* (2006.01)

(52) U.S. Cl.
USPC ............................................. 73/25.01; 95/90

(58) Field of Classification Search
USPC ........................................................ 73/25.01
See application file for complete search history.

(56) References Cited

U.S. PATENT DOCUMENTS

2009/0113991 A1\* 5/2009 Saito et al. ................... 73/31.02

FOREIGN PATENT DOCUMENTS

| JP | 2000-053992 | | 2/2000 |
| JP | 2000-266646 | | 9/2000 |
| JP | 2003-130860 | | 5/2003 |
| JP | 2006-518468 | | 8/2006 |
| JP | 2009-198224 | | 9/2009 |
| JP | 201049763 A | * | 3/2010 |
| WO | 03/048738 | | 6/2003 |

OTHER PUBLICATIONS

Japanese Office Action dated Aug. 7, 2012, filed in Japanese counterpart Application No. 2011-129780, 4 pages (including translation).

\* cited by examiner

*Primary Examiner* — Hezron E Williams
*Assistant Examiner* — Gregory J Redmann
(74) *Attorney, Agent, or Firm* — Patterson & Sheridan, LLP

(57) ABSTRACT

According to one embodiment, a generated gas collecting method collects a generated gas after exposing the interior of a chamber to an organic gas having a boiling point higher than that of the generated gas.

6 Claims, 5 Drawing Sheets

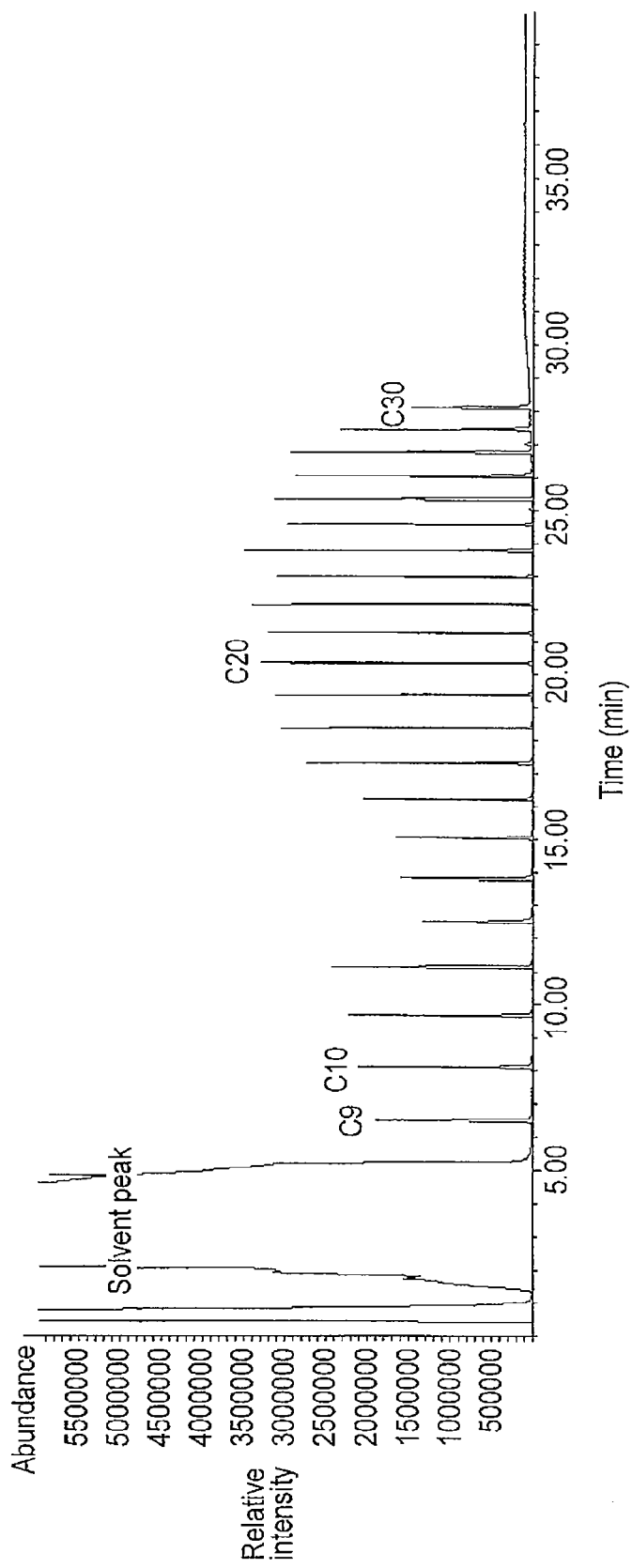
F I G. 4

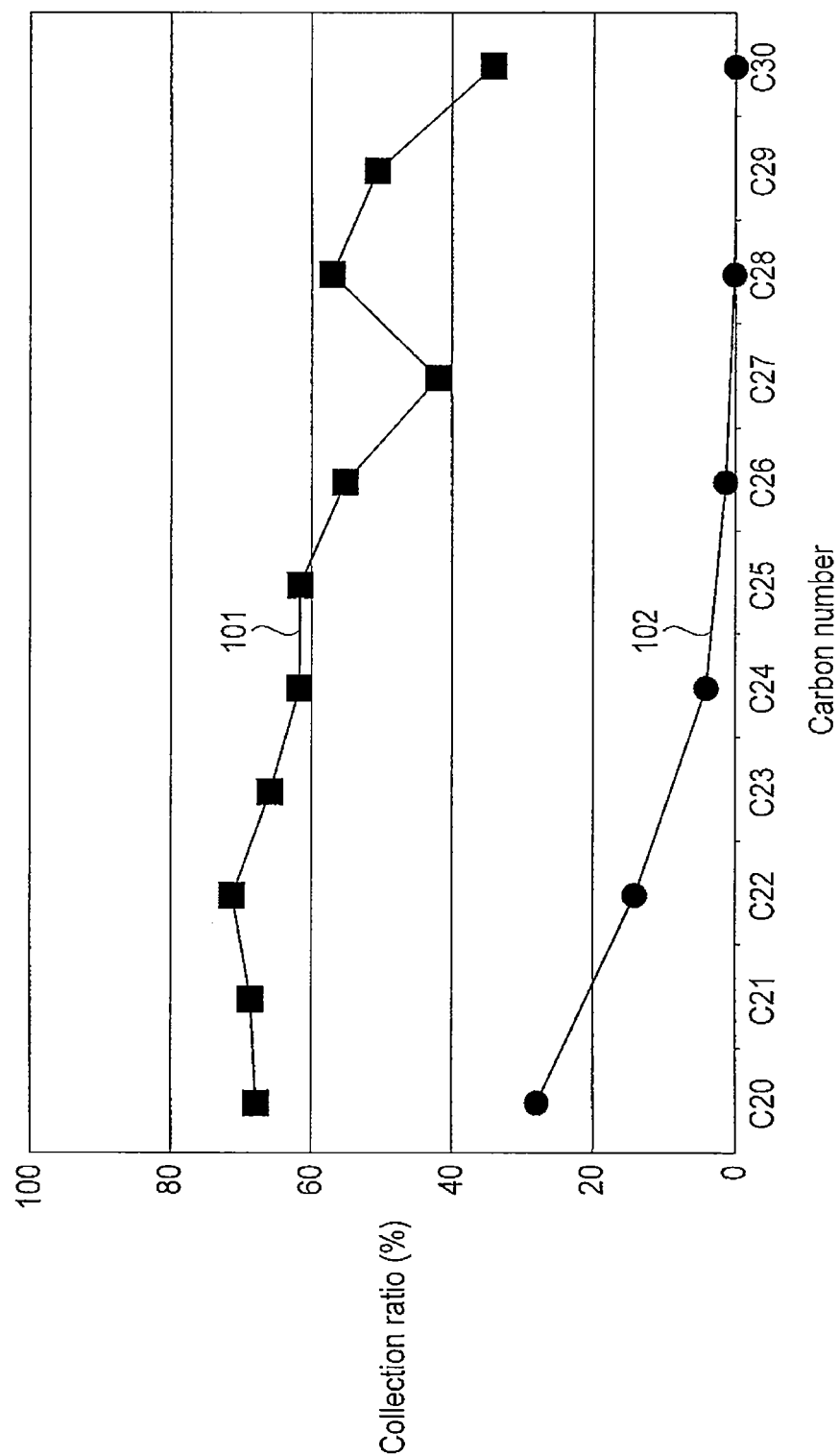
F I G. 6

GENERATED GAS COLLECTING METHOD AND MEASURING METHOD

CROSS-REFERENCE TO RELATED APPLICATIONS

This application is based upon and claims the benefit of priority from prior Japanese Patent Application No. 2011-122780, filed May 31, 2011, the entire contents of which are incorporated herein by reference.

FIELD

Embodiments described herein relate generally to a method of collecting a gas generated inside an electronic device or the like.

BACKGROUND

When a magnetic disk device is repetitively used, generated gases deriving from a part, lubricant, and the like used in the disk device and containing organic materials are released. The released generated gases gradually deposit on undesirable places in the device, e.g., between a read/write element of a head and the surface of a disk medium, and in the periphery. The generated gases cause problems, e.g., sliding of the head and changes to its floating posture, thereby deteriorating the reliability of the disk device.

Recently, the adverse effect of a generated gas like this on a magnetic disk device is increasing as the density of the device increases and the downsizing of the device advances.

Under the circumstances, it has become necessary to check even a slight amount of a generated gas released from, e.g., a part of a magnetic disk device in its use environment.

Unfortunately, it is difficult for a conventional collecting method to collect a slight amount of about 10 ng of a hydrocarbon component containing carbon exceeding, e.g., a carbon number of 24, and the collection ratio is less than 5%. In particular, a hydrocarbon equal to or higher than a carbon number of 28 or more is equal to or less than the detection limit, so the collection ratio is 0%.

The collection ratio can be increased by raising the heating temperature of a chamber. In reality, however, this method is sometimes inappropriate because the temperature cannot be raised due to the material of the packing of the chamber or there is a component that thermally decomposes if the temperature is excessively raised.

As described above, there is no conventional method capable of efficiently collecting a slight amount of a gas generated from, e.g., a part of a magnetic disk device without raising the temperature of a sample, and this makes the analysis of a generated gas difficult.

BRIEF DESCRIPTION OF THE DRAWINGS

A general architecture that implements the various features of the embodiments will now be described with reference to the drawings. The drawings and the associated descriptions are provided to illustrate the embodiments and not to limit the scope of the invention.

FIG. 4 is a graph showing an example of mass spectrometric data of a standard sample;

FIG. 6 is a graph showing examples of the collection ratios of hydrocarbon components.

DETAILED DESCRIPTION

Various embodiments will be described hereinafter with reference to the accompanying drawings.

In general, according to one embodiment, a generated gas collecting method includes the steps of placing a sample in a chamber, supplying a carrier gas into the chamber while heating the sample, carrying a generated gas from the chamber to an adsorption portion, and adsorbing the generated gas to an adsorption member formed in the adsorption portion, wherein before the sample is placed in the chamber, the interior of the chamber is exposed to an organic gas having a boiling point higher than that of the generated gas.

In this embodiment, an organic gas having a boiling point higher than that of a generated gas to be collected is applied beforehand into a chamber to be used. Therefore, the generated gas does not stay in the chamber and can be collected as it is efficiently carried to the adsorption portion and adsorbed by the adsorption member.

The organic gas having a boiling point higher than that of a generated gas to be collected generally has a vapor pressure lower than that of the generated gas to be collected. When using this organic gas, therefore, components dispersed and deposited inside the chamber are not easily removed. This presumably makes it possible to maintain the effect of efficiently adsorbing the generated gas to the adsorption member.

The embodiment will be explained below with reference to the accompanying drawings.

Figure 1:
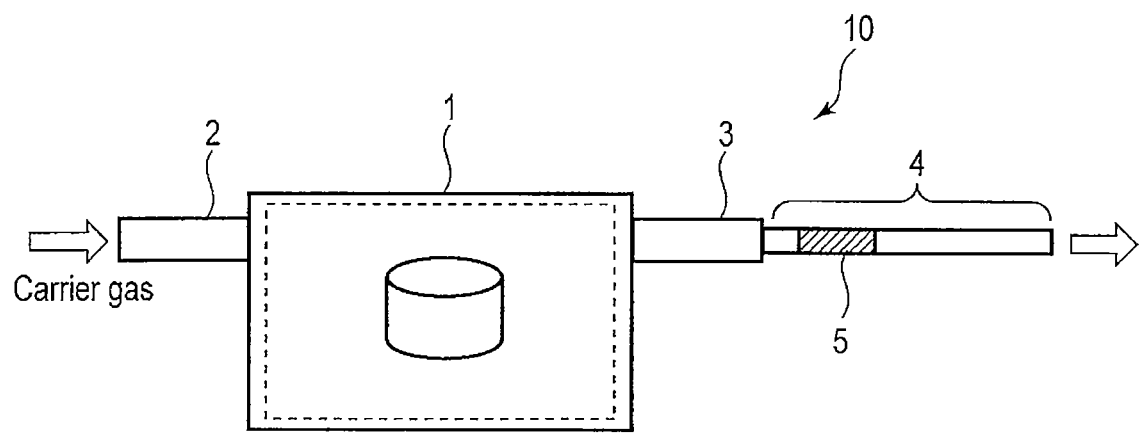
FIG. 1 is a schematic view showing an example of a collecting apparatus for performing a collecting method according to an embodiment.

FIG. 1 is a schematic view showing an example of a collecting apparatus for performing the collecting method according to the embodiment.

As shown in FIG. 1, a collecting apparatus 10 includes a chamber 1 having an air supply portion 2 and air exhaust portion 3, and an adsorption portion 4 connected to the air exhaust portion 3 and including an adsorption member 5. The chamber 1 is arbitrarily deactivated by coating the inner surfaces with gold. Alternatively, the chamber 1 is arbitrarily formed by using quartz.

A single adsorption layer, an adsorption tube packed with a plurality of adsorbents, or the like can be used as an adsorption member.

Figure 2:
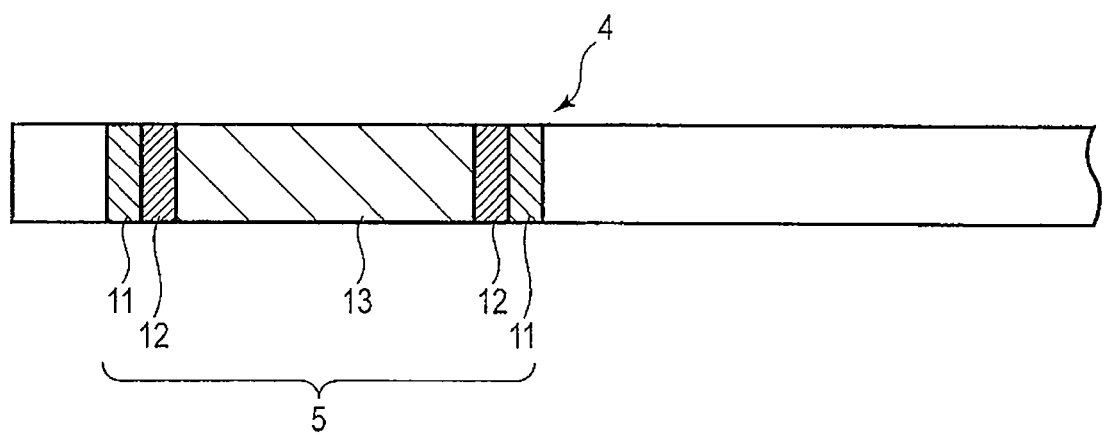
FIG. 2 is an enlarged view of an adsorption portion shown in FIG. 1.

FIG. 2 is an enlarged view of the adsorption portion shown in FIG. 1.

As shown in FIG. 2, the adsorption portion 4 includes the adsorption member 5.

The adsorption member 5 has an arrangement in which, for example, an adsorbent is placed in a cylindrical hollow tube made of glass or stainless steel, and the two ends are closed with meshes made of quartz wool or stainless steel, thereby arranging a mesh 11, quartz wool 12, an adsorbent 13, quartz wool 12, and a mesh 11 in this order. Alternatively, one end of the hollow tube is made of a material like a mesh sintered with glass, thereby preventing the removal of the adsorbent.

As the adsorbent, it is possible to use 100 mg of 20/35-mesh TenaxTA® (manufactured by GL Sciences). Other examples are TenaxGR, Carbotrap, Carboxen1000, Carbopack B, and Carbosieve S-III (all manufactured by Supelco). For example, TenaxTA itself is a porous resin containing a 2,6-diphenylen oxide polymer (having a surface area of 35 m²/g) as a base. Also, TenaxGR is obtained by adding 20% to 30% of carbon to TenaxTA.

Examples of the gas to be collected are gases generated by general products, parts, and constituent materials such as parts used in a magnetic disk device, semiconductors and their related products and constituent materials, construction members and interior materials of buildings, and interior materials of automobiles. An example of these generated gases is alkane gas represented by $C_nH_{2n+2}$ (n is less than 40) having a carbon number of about 7 to 34. An example of an organic gas having a boiling point higher than that of this generated gas is $C_{40}H_{82}$. These hydrocarbons can be collected by a thermal desorption system including an adsorbent and thermal desorption GC/MS.

A large number of gases from low-boiling-point components to high-boiling-point components are generated from inside a magnetic disk device. When the surface of an internal magnetic head of a faulty device was analyzed, a component having the molecular amount of hydrocarbon having a carbon number of 20 or more was found deposited on the surface. To eliminate a fault, therefore, it is necessary to evaluate a gas generated from an internal part of a magnetic disk device, specify the generation source, and take countermeasures. If the collection ratio of a hydrocarbon having a carbon number of 20 or more is low, the final analytical sensitivity decreases, so it is desirable to increase this collection ratio.

Also, the higher the chamber temperature, the more easily a gas is released. However, the material thermally decomposes and hence cannot be collected as the original material in some cases. Therefore, an organic gas having a high boiling point is applied.

Furthermore, a generated gas analyzing method according to the embodiment includes the step of supplying a carrier gas into a chamber while heating the interior of the chamber, bringing the carrier gas from the chamber into contact with an adsorption member formed in an adsorption portion, and analyzing an organic component in the adsorption member, thereby obtaining a first organic component analytical value, the step of placing a sample in the chamber, supplying a carrier gas into the chamber while heating the sample, bringing the carrier gas from the chamber into contact with the adsorption member formed in the adsorption portion, and analyzing an organic component in the adsorption member, thereby obtaining a second organic component analytical value, and the step of obtaining an organic component analytical value of the generated gas from the difference between the first and second organic component analytical values, wherein the method includes the step of exposing the interior of the chamber to an organic gas having a boiling point higher than that of the generated gas, before the sample is placed in the chamber.

Figure 3:
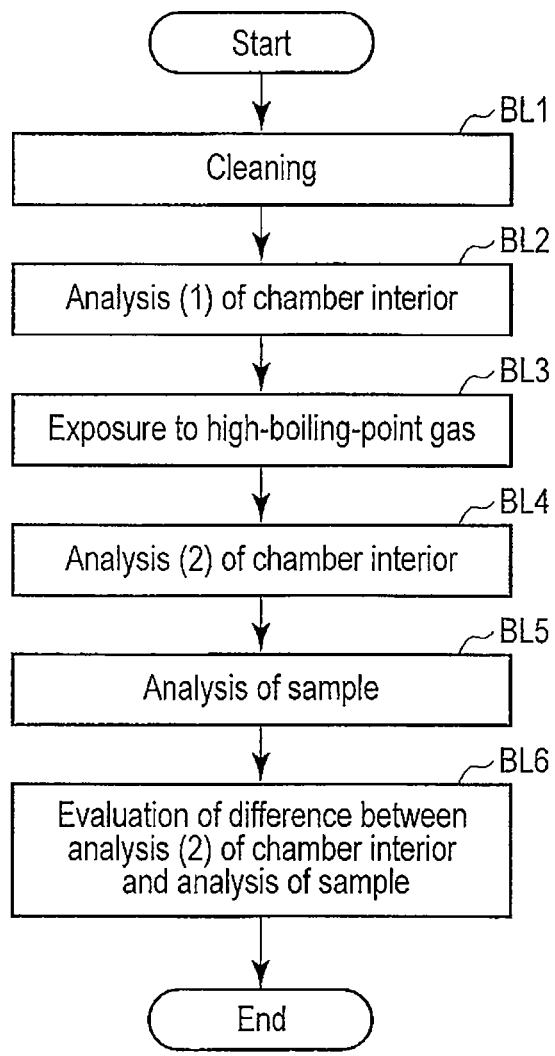
FIG. 3 is a flowchart showing an example of a generated gas analyzing method according to the embodiment.

FIG. 3 is a flowchart showing an example of the generated gas analyzing method according to the embodiment.

As shown in FIG. 3, the interior of a chamber is first cleaned by, e.g., supplying a solvent into the chamber and heating it (BL1).

After that, the chamber is heated from, e.g., 30° C. or less to 250° C., and collection is performed for 30 min from the start of the heating while a carrier gas is supplied from the air supply port at a flow rate of, e.g., 100 mL/min. The heating is stopped after the elapse of 30 min. When the chamber temperature has decreased from 250° C. to 30° C. or less (when 10 minutes have elapsed after the stoppage of the heating), the carrier gas is stopped, and the adsorption tube is detached. The detached adsorption tube is analyzed by the thermal desorption GC/MS method. This process is repeated until the generated gas in the chamber becomes constant (BL2).

A high-boiling-point gas material, e.g., $C_{40}H_{82}$ is applied into the chamber and gasified by heating the chamber at 250° C. for 1 hr while supplying a carrier gas, thereby exposing the interior of the chamber to $C_{40}H_{82}$ gas (BL3).

Subsequently, a generated gas when only the chamber interior is heated is analyzed in the same manner as in BL2 (BL4).

Furthermore, a sample is placed in the chamber, and a generated gas when the sample is heated is analyzed in the same manner as in BL2 (BL5).

Evaluation is performed by calculating the difference between the analytical value of the generated gas when the sample is heated and that of the generated gas when only the chamber interior is heated (BL6).

The embodiment will be explained in more detail below by way of its examples.

EXAMPLE 1

An apparatus having the same arrangement as that shown in FIG. 1 is prepared.

The interior of the chamber is deactivated by gold coating.

Also, the absorbent is, e.g., TenaxTA.

To collect hydrocarbons up to $C_{30}H_{62}$ as generated gases, the interior of the chamber is exposed to $C_{40}H_{82}$ that is the same system as $C_{30}H_{62}$ and has a high boiling point.

Exposure of Chamber Interior to High-Boiling-Point Gas

First, pre-processing is performed.

A magnetic disk is placed in the chamber.

While a carrier gas is supplied, the chamber is heated to 250° C. for an arbitrary time.

The adsorption tube containing the adsorbent is baked at 300° C. for about 1 hr while nitrogen or He gas is supplied, and analyzed under the same conditions as sample measurement conditions, thereby confirming that the adsorption tube is clean. If the adsorption tube is not clean, the tube is baked and analyzed again.

The chamber is heated from 30° C. or less to 250° C., and collection is performed for 30 min from the start of the heating while a carrier gas is supplied at a flow rate of 100 mL/min. After the elapse of 30 min, the heating is stopped. When 10 minutes have elapsed from the stoppage of the heating and the internal temperature of the chamber has decreased from 250° C. to 30° C. or less, the carrier gas is stopped, and the adsorption tube is detached.

The detached adsorption tube is analyzed by the thermal desorption GC/MS method.

The process is repeated until the generated gas from the chamber and magnetic disk becomes constant.

For example, conditioning is performed at 250° C. for about 3 hrs at a carrier gas flow rate of 100 mL/min.

It is confirmed that no peak is detected except for peaks pertaining to the measurement system.

The confirmed adsorption tube is attached to the heated chamber.

Again, the chamber is heated from 30° C. or less to 250° C., and collection is performed for 30 min from the start of the heating while a carrier gas is supplied at a flow rate of 100 mL/min. After the elapse of 30 min, the heating is stopped. When 10 minutes have elapsed from the stoppage of the heating and the internal temperature of the chamber has decreased from 250° C. to 30° C. or less, the carrier gas is stopped, and the adsorption tube is detached.

The detached adsorption tube is analyzed by the thermal desorption GC/MS method.

The process is repeated until the generated gas from the chamber and magnetic disk becomes constant.

The foregoing is the pre-processing.

After the generated gas has become constant, about 1 mg of $C_{40}H_{82}$ is placed on the magnetic disk surface, and the chamber is heated to 250° C. for 1 hr while a carrier gas is supplied.

The magnetic disk is taken out with $C_{40}H_{82}$ remaining on it. The magnetic disk surface is coated with $C_{40}$ by placing it on the surface and then the disk is taken out because if $C_{40}$ is directly placed inside the chamber, the amount of generated gas may become excessive and obstructive.

Preparations for Generated Gas Collection

While a carrier gas is supplied, the chamber is heated to 250° C. for an arbitrary time.

Also, generated gas analysis is performed on the chamber alone. That is, the chamber is heated from 30° C. or less to 250° C., and collection is performed for 30 min from the start of the heating while a carrier gas is supplied at a flow rate of 100 mL/min. After the elapse of 30 min, the heating is stopped. When 10 minutes have elapsed from the stoppage of the heating and the internal temperature of the chamber has decreased from 250° C. to 30° C. or less, the carrier gas is stopped, and the adsorption tube is detached.

It is confirmed that nothing is detected except for the peak and decomposed product of $C_{40}H_{84}$, a peak deriving from the chamber, and a peak pertaining to the measurement system.

The chamber is repetitively baked until the peaks other than $C_{40}H_{84}$ become constant.

After it is confirmed that the peaks other than $C_{40}H_{84}$ have become constant, an actual sample collecting operation starts.

Procedures of Collecting and Analyzing Generated Gas from Sample

Immediately before sample collection, a generated gas from the chamber alone is necessarily collected and analyzed, thereby confirming that $C_{40}H_{84}$ is detected, and checking a generated gas from the chamber (blank measurement).

After this blank measurement, an actual sample is placed in the chamber.

The chamber is heated from 30° C. or less to 250° C., and collection is performed for 30 min from the start of the heating while a carrier gas is supplied at a flow rate of 100 mL/min. After the elapse of 30 min, the heating is stopped. When 10 minutes have elapsed from the stoppage of the heating and the internal temperature of the chamber has decreased from 250° C. to 30° C. or less, the carrier gas is stopped, and the adsorption tube is detached.

The detached adsorption tube is analyzed by the thermal desorption GC/MS method.

Quantitation—Standard Sample Measurement

The adsorption tube containing the adsorbent is baked at 300° C. for about 1 hr while nitrogen or He gas is supplied, and analyzed under the same conditions as sample measurement conditions, thereby confirming that the adsorption tube is clean. If the adsorption tube is not clean, the tube is baked and analyzed again.

As standard samples, alkane components each diluted by n-hexane at a concentration of 10 ng/μL are prepared. In each alkane component, the carbon number of the hydrocarbon is an even number of 10 to 30.

A microsyringe is cleaned with n-hexane used to dilute the hydrocarbon of each standard sample.

The microsyringe is washed with the standard sample.

One μL of the standard sample is sampled, and spiked against the adsorbent of the adsorption tube.

Measurement is rapidly performed by the thermal desorption GC/MS method under the same conditions as measurement conditions.

FIG. 4 shows an example of mass spectrometric data.

Mass Spectrometric Data

Note that in FIG. 4, the relative intensity plotted on the ordinate is equivalent to a relative value with respect to the current intensity, because the detected sample has an electric charge in the form of ions.

The same operation is repeated several times.

The average value of the obtained peak areas is calculated. Consequently, the area count/ng per unit mass of the standard sample used is obtained.

To calculate the quantitative value of the $C_{20}$ component from the sample measurement results, the amount of generated gas can be calculated from the peak area count of the sample and the coefficient of the area count/ng of the $C_{20}$ component when the standard sample is measured. If the target peak component and the component used as a standard are the same, nothing is particularly specified. If the two components are different, however, the obtained value is a value converted from the standard component, so it is specified that the value is converted from the component used.

The generated gas amount is represented by

Generated gas amount (ng)=peak area count of target component of sample÷(peak area count of target component of standard sample÷mass of target component of standard sample)

Quantitation Correction—Collection Ratio

The collection ratio changes from one component to another. Therefore, a known amount of a target component itself or a component whose retention time (R.T) is close to that of the target component on a chromatogram is placed on a magnetic disk in the chamber pre-processed following the procedures of the pre-processing of exposing the chamber interior to a high-boiling-point gas.

Then, a known amount (the same amount as that in the quantitation—standard sample measurement) of the component as a target of collection ratio calculation is spiked on the magnetic disk.

After that, collection and measurement are performed in the same manner as for a sample.

Figure 5:
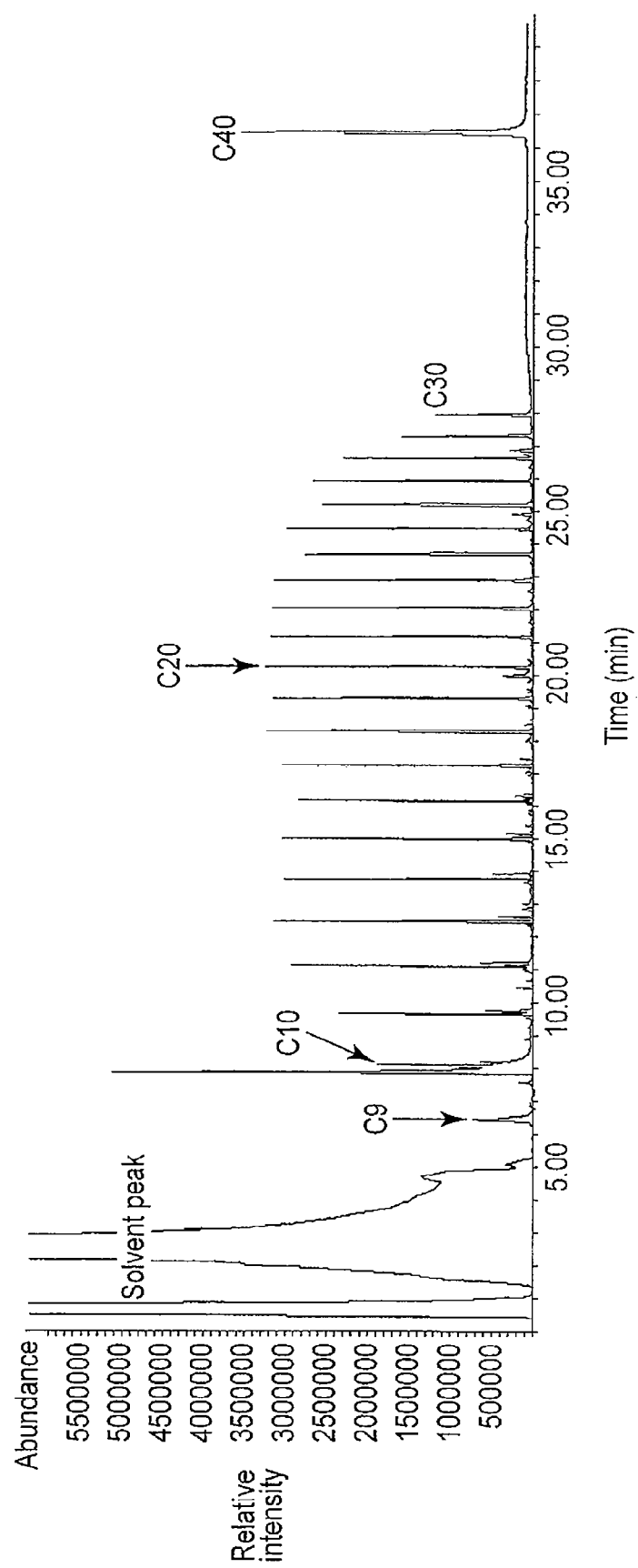
FIG. 5 is a graph showing an example of mass spectrometric data of a collection ratio checking sample.

FIG. 5 shows an example of the measured mass spectrometric data.

As shown in FIG. 5, the peaks of hydrocarbons having carbon numbers of $C_9$ to $C_{30}$ clearly appear together with that of $C_{40}$. This demonstrates that the hydrocarbons are sufficiently collected by the adsorption member.

The result is compared with that previously obtained in the quantitation—standard sample measurement, and the ratio is obtained by using the result of the quantitation—standard sample measurement as a denominator.

Note that another measurement is performed if the component used to check the collection ratio is not used as the standard sample.

An actual generated gas amount is calculated by multiplying the generated gas amount by the collection ratio of the target component.

The collection ratio is represented by

Collection ratio (%)=(peak area count of target component in quantitation correction–collection ratio/peak area count of target component in quantitation–standard sample measurement)×100

FIG. 6 shows an example of improvement.

Referring to FIG. 6, the collection ratio of 10 ng of a component of each of hydrocarbons having even carbon numbers from $C_{20}$ to $C_{30}$ was measured. A curve 101 indicates the example in which the chamber interior was exposed to $C_{40}H_{82}$ before sample measurement. A curve 102 indicates a comparative example in which the chamber interior was not exposed to $C_{40}H_{82}$. The collection ratio of each hydrocarbon after $C_{24}$ was less than 5% in the comparative example, but increased to 30% or higher in the example.

EXAMPLE 2

To collect plasticizers (examples of plasticizers mainly used in the past are diethyl phthalate (DEP), dibutyl phthalate (DBP), and dioctyl phthalate (DEHP)) up to dioctyl phthalate (DEHP) as generated gases, the interior of the chamber is exposed to diisononyl phthalate that is the same system as phthalic acid ester and has a high boiling point.

After that, the amount and collection ratio of a generated gas can be calculated by performing measurements in the same manner as for hydrocarbons in Example 1.

Consequently, a peak appears in R.T similar to $C_{26}$. That is, the collection ratio of DEHP increases, even though DEHP is a polar material and hence is readily adsorbed to the chamber inner walls and has a low collection ratio when compared to $C_{26}$.

In these embodiments or examples as described above, the interior of a chamber is pre-exposed to a component that is the same system as a component to be measured and has a boiling point higher than that of the component to be measured. This makes it possible to measure a target component at a higher collection ratio. It is sometimes possible to measure a component having been immeasurable.

Although several embodiments of the present invention have been explained, these embodiments are presented as examples, and are not intended to limit the scope of the invention. These novel embodiments can be practiced in a variety of other forms, and various omissions, substitutions, and changes can be made without departing from the spirit and scope of the invention. These embodiments and their modifications are incorporated in the spirit and scope of the invention, and are also incorporated within the range of inventions described in the scope of claims and their equivalents.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A generated gas collecting method, comprising:
exposing an interior of a chamber to an organic gas that comprises $C_{40}H_{82}$, the organic gas having a boiling point that is higher than a boiling point of a generated gas that is generated from a sample to be placed in the chamber;
placing the sample in the chamber;
supplying a carrier gas into the chamber while heating the sample in the chamber, and
bringing the carrier gas and the generated gas that has been generated from the sample in the chamber into contact with an adsorption member.

2. The method of claim 1, wherein a material of at least an inner surface of the chamber is one of gold and quartz.

3. The method of claim 1, wherein the generated gas comprises a hydrocarbon represented by $C_nH_{2n+2}$ (n is less than 40).

4. The method of claim 3, wherein n is 7 to 34.

5. The method of claim 1, wherein the adsorption member is a porous resin.

6. The method of claim 1, wherein the adsorption member is formed in an adsorption portion.

* * * * *